United States Patent [19]

Schmoegner et al.

[11] Patent Number: 4,770,169
[45] Date of Patent: Sep. 13, 1988

[54] ANAESTHETIC MASK

[75] Inventors: John C. Schmoegner, Redondo Beach; Charles B. Swenson, Palos Verde Penninsula; J. Miles Branagan, Palos Verde Estates, all of Calif.

[73] Assignee: MDT Diagnostic Company, Torrance, Calif.

[21] Appl. No.: 14,394

[22] Filed: Feb. 13, 1987

[51] Int. Cl.[4] .................. A62B 18/02; A62B 18/08
[52] U.S. Cl. ..................... 128/207.13; 128/206.28; 128/206.24; 128/910
[58] Field of Search .............. 128/203.12, 203.29, 128/205.25, 205.19, 204.18, 207.13, 206.28, 206.26, 206.24, 206.21, 910

[56] References Cited

U.S. PATENT DOCUMENTS

| | | | |
|---|---|---|---|
| 1,362,766 | 12/1920 | McGargill | 128/206.24 |
| 2,939,458 | 6/1960 | Lundquist | 128/206.24 |
| 3,343,535 | 9/1967 | Lytle et al. | 128/206.24 |
| 3,799,164 | 3/1974 | Rollins | 128/205.25 |
| 3,877,691 | 4/1975 | Foster | 128/132 R |
| 4,015,598 | 4/1977 | Brown | 128/205.25 |
| 4,062,357 | 12/1977 | Laerdal | 128/206.26 |
| 4,151,843 | 5/1979 | Brekke et al. | 128/205.25 |
| 4,219,020 | 8/1980 | Czajka | 128/207.13 |
| 4,248,218 | 2/1981 | Fischer | 128/204.18 |
| 4,265,239 | 5/1981 | Fischer, Jr. et al. | 128/207.13 |
| 4,312,339 | 1/1982 | Thompson, Sr. | 128/205.25 |

Primary Examiner—William E. Kamm
Assistant Examiner—Timothy G. Philips
Attorney, Agent, or Firm—Trask, Britt & Rossa

[57] ABSTRACT

The present invention provides an improved anaesthetic scavenging face mask having a scavenging channel running along the perimeter of the mask. The mask is provided with an anaesthetic gas inlet and a vacuum outlet. The scavenging channel is connected to the vacuum outlet.

22 Claims, 5 Drawing Sheets

ANAESTHETIC MASK

BACKGROUND OF THE INVENTION

1. Field

The present invention relates to an improved anaesthetic scavenging face mask and more particularly, to an improved anaesthetic mask having a scavenging channel formed along the perimeter of the respiratory chamber.

2. State of the Art

Anaesthetic gases have been used on medical and dental patients advantageously for years. For example, U.S. Pat. No. 2,254,854 (O'Connell), discloses a face mask having two anaesthetic gas supply inlets and an outlet valve which allows exhaled gases to be vented into the operating room.

It has become apparent that the escape of anaesthetic gases into the operating room may have deleterious health effects. For example, there may be a tendency for the dentist, doctor or other medical personnel to become anaesthetized. Also, studies have shown that exposure to the commonly used anaesthetic gas nitrous oxide may increase the risk of certain serious diseases. Exposure of nitrous oxide to pregnant personnel may also involve an increased rate of spontaneous abortion or a higher incidence of birth defects.

Various patents disclose devices which attempt to deal with the problem of anaesthetic gases in the operating room. For example, U.S. Pat. No. 3,721,239 (Myers) discloses a suction driven exhaust system which draws off anaesthetic gases from the pop-off or vent valve of the air suction system. This patent, therefore, deals with problems of escaping anaesthetic gases remote from the face mask. U.S. Pat. No. 3,877,691 (Foster) discloses an arcuate barrier or shield having a plurality of holes on the underside. The shield acts as a barrier between the patient and the medical practitioner, and the plurality of holes are connected to a vacuum source to vent exhaled gases to a remote location.

U.S. Pat. No. 4,015,598 (Brown) discloses an anaesthetic system utilizing a double-wall mask. A vacuum source is connected to the space between the interior and exterior wall of the anaesthetic mask. The space along the rim of the mask between the inner and outer wall scavenges leaking gases. Brown also discloses a transparent mask. U.S. Pat. No. 4,219,020 (Czajka) discloses a scavenger valve attachment. This attachment is mounted on a typical anaesthetic face mask in place of a conventional exhalation valve, and includes a vacuum chamber having an annular aperture, or one or more small apertures, formed in a pair of substantially frustoconically shaped members which radiate outward from the valve body and which are spaced apart from each other to define an annular exhaust chamber.

U.S. Pat. No. 4,265,239 (Fischer, Jr. et al.) discloses a gas scavenging exhaust system which includes a peripheral exhaust chamber, which, similar to Brown U.S. Pat. No. 4,015,598, is shown to be a space between an inner and outer wall of the mask. Between the inner and outer wall are bumps which act as a spacer means to keep the peripheral exhaust chamber from collapsing under the influence of the vacuum. U.S. Pat. No. 4,312,339 (Thompson, Sr.) discloses a mask with a pair of suction nozzles which scavenge gas escaping from the mask. These nozzles are illustrated as terminating on the sides of the mask in front of the inlet and outlet tubes.

U.S. Pat. No. 4,151,843 (Brekke) discloses two separate embodiments of a nose mask. One embodiment includes a mask having an interior cavity and a pair of nasal cannulas attached to the gas flow control. Anaesthetic and exhaust gases pass from the flow control to the cannulas and vice versa through a hollow space in the mask. The second embodiment has two tubes, each of which has a compressible cuff on the nostril end for the purpose of forming a positive seal between the patient's nostril and the tube. U.S. Pat. No. 4,248,218 (Fischer) discloses a nose piece with a pair of tubes for connection to a patient's nostrils. The outer nose piece scavenges anaesthetic exhaust gases exhaled from the patient's nostrils or escaping from the tubes. The nose piece also has a plurality of holes on the underside to scavenge gases exhaled from the patient's mouth. The nose piece has a single gas supply tube and a single vacuum supply tube.

Also known are systems having on-demand gas supply, and vacuum systems which become operative to the interior of the face mask only upon exhalation of the patient, and which, nevertheless, maintain a continuous vacuum supply to the scavenging function of the mask. Also existent are systems having a slight suction effect within the respiration chamber of the mask which tends to hold the mask against the face to maintain the integrity of the seal between the mask and the face.

SUMMARY OF THE INVENTION

A mask of the present invention includes a respiratory chamber having a perimeter sized and configurated to generally conform to a selected area surrounding the nose or mouth of a patient. The perimeter of the chamber thus effects a seal with the face of a patient. A gas inlet is associated with the respiratory chamber for connection to an anesthetic gas supply, and an exhaust outlet is associated with the respiratory chamber for connection with a vacuum supply. A scavenging channel is carried by the respiratory chamber at its perimeter, and a vacuum communication means is in open communication with the scavenging channel for providing gas intercommunication between the scavenging channel and the vacuum supply.

The mask may also include a face seal (which may be removable) carried by and thus constituting a structural element of the perimeter of the respiratory chamber. In one embodiment, the scavenging channel may be characterized as a tubular enclosure proximate the peripheral edge of the chamber. The scavenging channel may be formed entirely within the seal.

Another embodiment of the present invention provides an improved anaesthetic face mask having a scavenging channel around the rim of the face mask, which scavenging channel is enclosed within the peripheral edge of the mask and positioned to be proximal to the face of a patient. A vacuum connection is provided between the scavenging channel and vacuum source, and the mask has a plurality of vacuum holes along the perimeter of the mask to scavenge any leaking gases. The peripheral edge of the mask may also have a plurality of sealing surfaces. When the face mask is worn, the space between the sealing surfaces and the patient's face provides enclosed channels, which may be characterized as additional scavenging channels or sealing channels and which may be connected to all or some of the previously mentioned vacuum holes.

The mask of the invention includes a respiratory chamber formed and is configured to achieve gas communication with the nose and/or mouth of a patient. The mask has a gas inlet to the respiratory chamber and a vacuum outlet connected to the respiratory chamber. Either the gas inlet and/or the vacuum outlet may be provided with suitable valves so that anaesthetic gas enters the mask only on inhalation of the patient and so that the vacuum opens only on exhalation of the patient. The mask of the present invention is adapted so that only a single gas supply and a single vacuum supply are needed. In addition, the mask may be formed of a transparent material.

The face mask of the present invention may include a transparent cup-shaped respiratory chamber adapted to fit over the nose and/or mouth of a patient. The mask may be provided with a grooved rim. Connected to this rim is a soft pliable face seal which connects with the mask by means of an orifice or groove in the seal enclosing the grooved rim of the respiratory chamber. The Y-shaped rim on the mask and the annular groove of the seal combine to form a tubular vacuum channel which connects independently to the vacuum supply.

A plurality of vacuum holes are formed in the seal and connected to the vacuum channel to scavenge leaking gases. The pliable face seal preferably has two sealing surfaces so that when the face mask is placed upon the face of a patient, the space between the sealing surfaces and the patient's face form an enclosed air channel. Preferably, the previously mentioned vacuum holes are connected to the enclosed air channel.

Face masks of the present invention, for a given amount of anaesthetic effect, typically use less anaesthetic gas and allow less anaesthetic gas to escape into the operating room than masks such as the type disclosed in Brown U.S. Pat. No. 4,015,598.

BRIEF DESCRIPTION OF THE DRAWINGS

The drawings illustrate what is currently regarded as the best mode for carrying out the invention.

DETAILED DESCRIPTION OF THE PREFERRED EMBODIMENT

Figure 1:
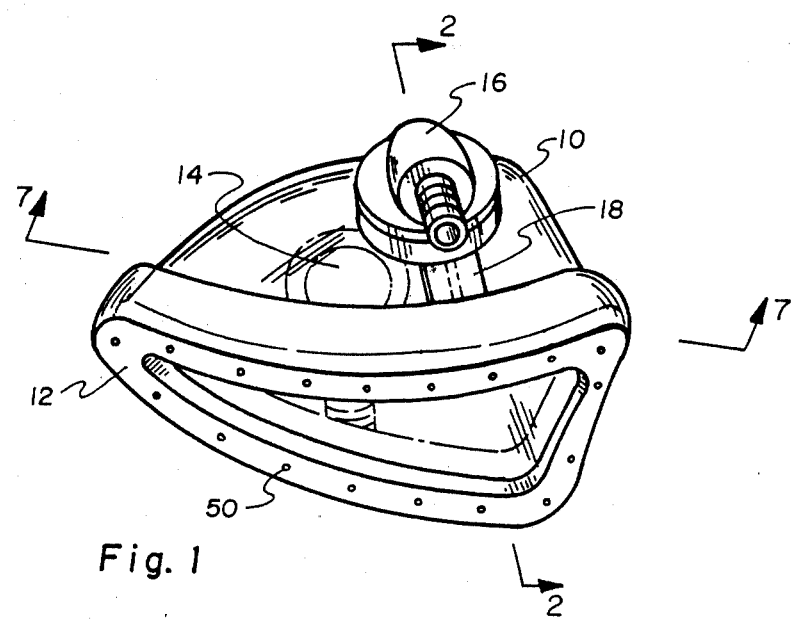
FIG. 1 is a perspective view of an anaesthetic mask of the invention.

As shown in FIG. 1, an anaesthetic face mask of the present invention includes a cup-shaped respiratory chamber 10, a face seal 12, an anaesthetic gas inlet 14, a vacuum outlet 16, and a connection channel or tube 18.

Figure 2:
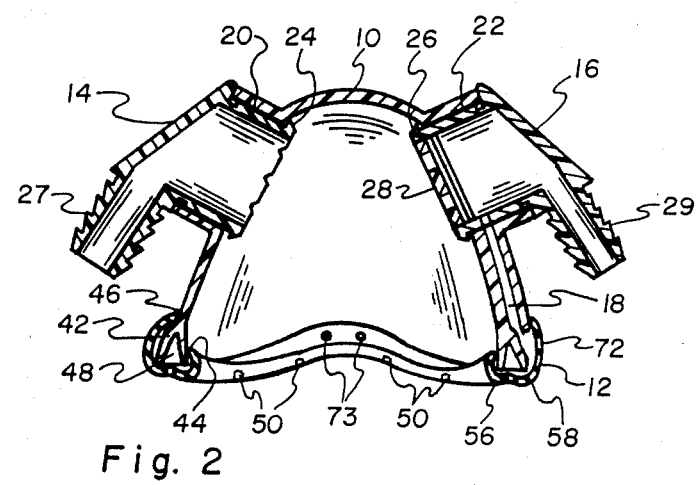
FIG. 2 is a section view of the mask of FIG. 1 taken along line 2—2 of FIG. 1.

FIG. 2 is a section view of the anaesthetic mask of FIG. 1 taken along line 2—2 of FIG. 1. The cup-shaped respiratory chamber 10 is formed of a rigid transparent, plastic-like material, typically polysulfone (Union Carbide P3500).

The inlet member 14 and the outlet member 16 connect with respiratory chamber 10 at circular openings 20 and 22, respectively, in respiratory chamber 10. The inlet member 14 and outlet member 16 clip to the respiratory chamber 10 by means of flexible flanges 24 and 26, respectively. Members 14 and 16 are typically formed of polysulfone. In use, inlet port 14 is connected at the rigid collar 27 to a typically constant anaesthetic gas supply of the proper composition and flow rate for the particular circumstances. Outlet member 16 has a valve 28 of a type which is common in the art which opens only upon exhalation of the patient. Outlet member 16 connects at rigid collar 29 to a vacuum supply.

The face seal 12 is formed (typically injection molded) of a soft pliable rubber-like material (typically sterilizable silicone such as sterilizable gray silicone, Shore A 50) so as to form an efficient seal when placed against a patient's face. The respiratory chamber 10 has a Y-shaped rim 42. The face seal 12 attaches to respiratory chamber 10 by means of the annular groove formed between edges 44 and 46 of face seal 12 enclosing the Y-shaped rim 42 of respiratory chamber 10. The space between face seal 12 and Y-shaped rim 42 comprises an annular scavenging channel 48 within face seal 12.

A cylindrical channel 18 is formed in respiratory chamber 10, as shown, to provide gas intercommunication between vacuum member 16 and the vacuum channel 48 formed in face seal 12. A plurality of vacuum holes 50 are formed in face seal 12 between sealing edges 56 and 58 and connected to vacuum channel 48. When the face mask is placed upon the face of a patient, the area between sealing surface 58 and 56 and the patient's face forms a secondary vacuum channel. Holes 50 scavenge exhaust gases which may escape beyond seal 56. Therefore, the area between ridges 56 and 58 define a scavenging channel, which is in addition to scavenging channel 48.

Figure 3:
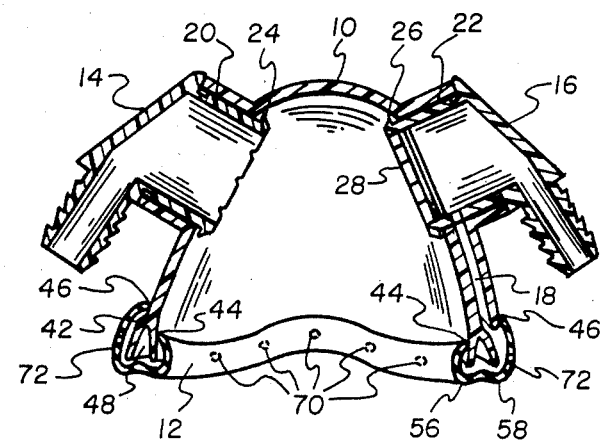
FIG. 3 is a section view of another embodiment of a mask of the invention.

FIG. 3 illustrates a section view of a mask identical to the mask of FIG. 2 except for the placement of holes 50 in the seal 12. Holes 50 are replaced by holes 70. Holes 70 connect the annular channel 48 with the outside edge 72 of seal 12 to scavenge gases which may escape beyond sealing edge 58 to the ambient air near a patient's face around the rim of the mask.

Referring again to FIG. 2 a plurality of holes 73 (in this embodiment, two holes) are formed in the outside edge 72, of the seal 12 to provide gas communication between the vacuum channel 48 and the ambient air. This plurality of holes 73 are positioned so as to be near the patient's mouth when the mask is used as a nose piece.

In operation, the face masks of FIGS. 1 and 2, or the face mask of FIG. 3, is placed over the nose area of a patient. While these embodiments are specifically adapted to be placed over the nose of a patient, it is to be understood that the face masks within contemplation of this invention would also function in a form which is to be placed over the mouth only or the mouth and nose of a patient, which may be of particular advantage in applications designed for infants or children.

Anaesthetic gas enters through inlet member 14 to the interior of the respiratory chamber 10, thereby allowing the patient to inhale the anaesthetic gases through his nose. When the patient exhales, through his nose the valve 28 opens, thereby allowing the exhaled exhaust gases to be removed through vacuum member 16 to a location remote from the patient and the operating room. Exhaust gases exhaled from the mouth are ideally sucked through holes 73 into the interior of vacuum channel 48, channel 18, and into exhaust member 16.

In the embodiment of FIGS. 1 and 2, exhaust gases which escape beyond sealing edges 56 are ideally swept into holes 50, into channel 48, through channel 18, into exhaust member 16, and thence to the remote location. Since the channel 18 is not in series with valve 28, the vacuum source is constantly supplied to channel 48 so that the holes 50 are constantly scavenging exhaust gases that may escape. Holes 50 are also positioned so as to create a suction between ridges 56 and 58 and the patient's face to improve the sealing qualities of the mask.

In the embodiment of FIG. 3, exhaust gases which escape beyond sealing ridge 58 are ideally swept through holes 70 into chamber 48, through chamber 18, into exhaust member 16, and thence to a remote location. Alternative embodiments may also have both holes 70 and holes 50. In other words, exhaust port holes may exist between ridges 56 and 58 and on the exterior 72 of face seal 12. Such an embodiment may advantageously create a suction between ridges 56 and 58 when the seal is placed against the patient's face and may also scavenge any gas which may leak beyond the ridge 58.

The seal 12 may be formed of a soft pliable material to allow it to be easily removed from respiratory chamber 10 and sterilized, or the seal 12 may be made of an inexpensive flexible material which may be disposable. An additional advantage of having the member 12 removable is that the doctor, dentist, or other practitioner may be able to select from a variety of types, shapes and sizes, etc., an appropriate seal 12 for the particular procedure or patient.

As discussed below with reference to FIG. 18, a strap may be formed of two belts connecting to the inlet and outlet members respectively. These belts may be formed of velcro or of other material having adhering properties, such as certain plastics having an adhering property.

As shown in the FIGS. 1-3 it is preferable for anaesthetic gas to be constantly supplied to the mask. In other words, there is no valve in the inlet member. However, the outlet member is valved in such a way that vacuum is supplied to the mask when the patient exhales. Also, the valve in the outlet member may be adjusted to open even when the patient does not exhale when pressure builds up inside the mask, for example, when all of the holes 50 are sealed and anaesthetic gas continues to enter the mask.

Figure 4:
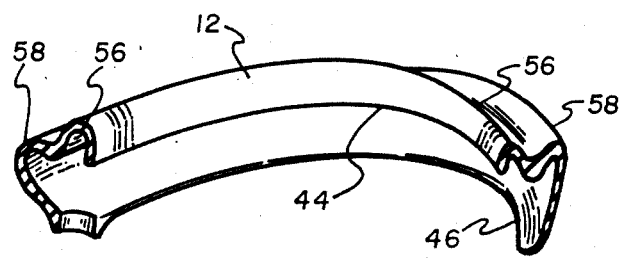
FIG. 4 is a partial cut-away view of a face seal of the invention.
Figure 6:
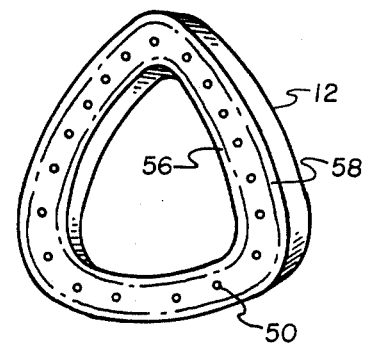
FIG. 6 is a bottom perspective view of a face seal of the invention.
Figure 5A:
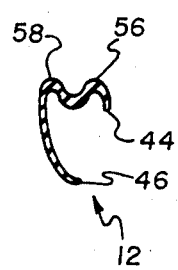
FIGS. 5A and 5B illustrate cross-sections of the face seal designated 12 in FIG. 4.
Figure 5B:
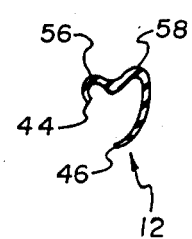

FIGS. 4 and 5 illustrate portions of seal 12 and depict sealing surfaces 56 and 58. Edges 44 and 46 associate with the perimeter of chamber 10. FIG. 6 illustrates a bottom view of seal 12 including a plurality of holes 50.

Figure 7:
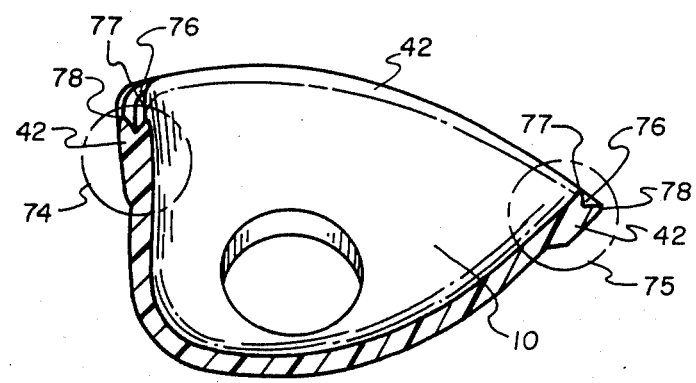
FIG. 7 is a sectional view of respiratory chamber 10 taken along line 7—7 of FIG. 1 as viewed from behind.
Figure 8:
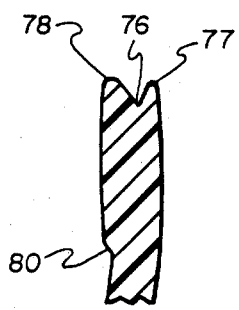
FIG. 8 is an expanded view of a portion designated 74 in FIG. 7.
Figure 9:
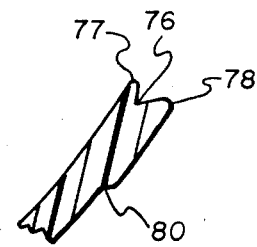
FIG. 9 is an expanded view of a portion designated 75 in FIG. 7.

FIG. 7 more clearly illustrates grooved rim 42. As best shown by FIGS. 8 and 9, rim 42 includes a groove 76 running along the perimeter of rim 42 which gives rim 42 its grooved shape to define ridges 77 and 78. As also more clearly shown in FIGS. 8 and 9, a boss 80 extends around the edge of chamber 10 to facilitate securement of the face seal 12 (see FIG. 2).

Figure 10:
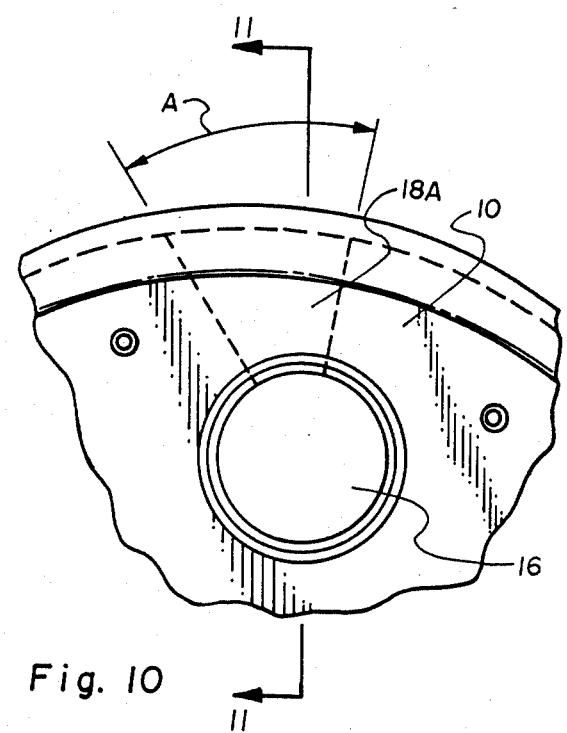
FIG. 10 is a partial cutaway view of an alternative embodiment.
Figure 11:
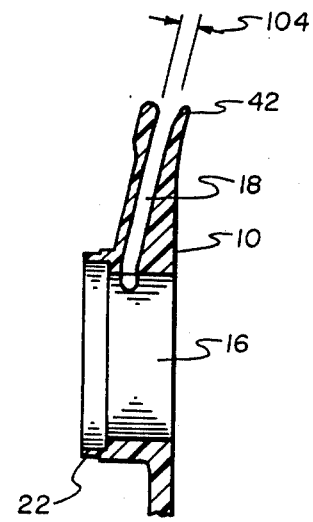
FIG. 11 is a sectional view taken along line 11—11 of FIG. 10.

FIGS. 10 and 11 illustrate details of an alternative embodiment of connection channel 18A. As shown in FIG. 10, connection channel 18A is of generally truncated triangular shape. Channel 18A occupies an included angle A, typically about 45°, and is shown with a typical cross-sectional width 104 of about 0.06 inches.

Figure 13:
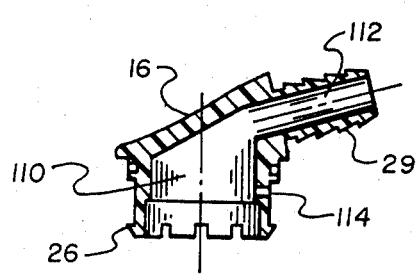
FIG. 13 is a sectional view of an outlet member of the invention.
Figure 12:
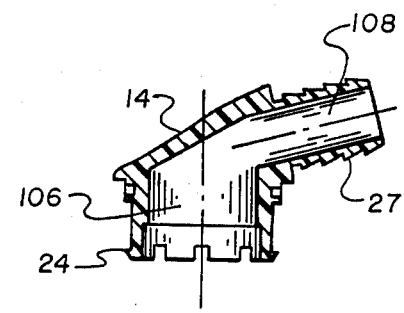
FIG. 12 is a sectional view of an inlet member of the invention.
Figure 14:
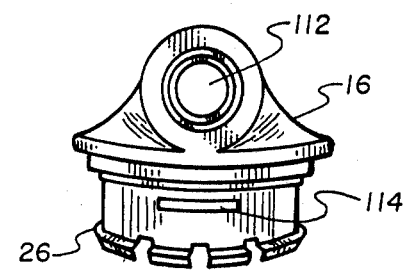
FIG. 14 is a plan view of the outlet member designated 16 in FIG. 11.

FIG. 12 illustrates details of inlet member 14. Typical diameter of interior channels 106 and 108 are about ⅜ and about 5/16 inch, respectively. FIGS. 13 and 14 show details of outlet member 16. Typical diameters of cylindrical channels 110 and 112 are about 6/8 and 7/32 inch, respectively. As shown in FIGS. 13 and 14, outlet member 16 has a channel 114 to allow air or gas communication between channel 18 and the interior of member 16. Members 14 and 16 rotatably associate with chamber 10.

Figure 16:
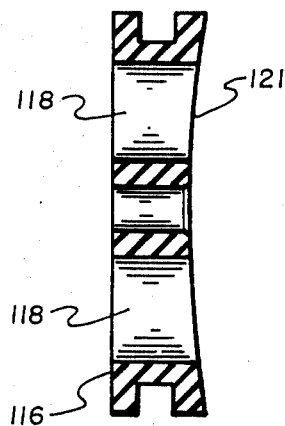
FIG. 16 is a sectional view of the flapper spool of FIG. 15 taken along line 16—16 of FIG. 15.
Figure 15:
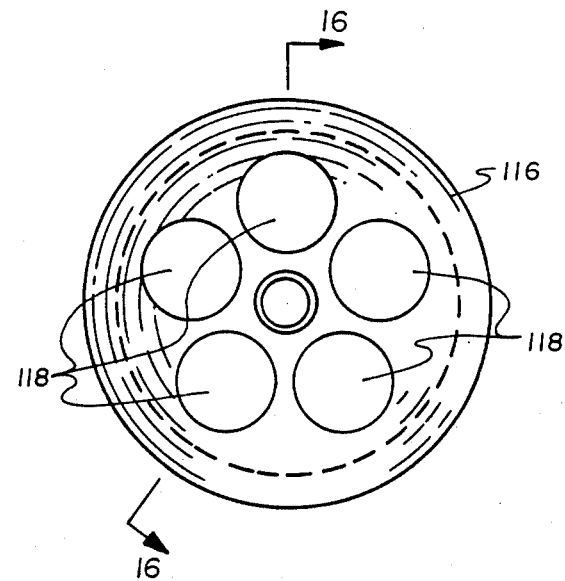
FIG. 15 is a plan view of a flapper spool of a valve of the invention.

FIGS. 15 and 16 illustrate details of a flapper valve spool 116 to be used in a valve such as valve 28. As shown, spool 116 has five generally cylindrical channels 118 formed in it. Spool 116 is typically formed of delrin or nylon. Surface 121 is typically curved with a radius of about 2 inches.

Figure 17:
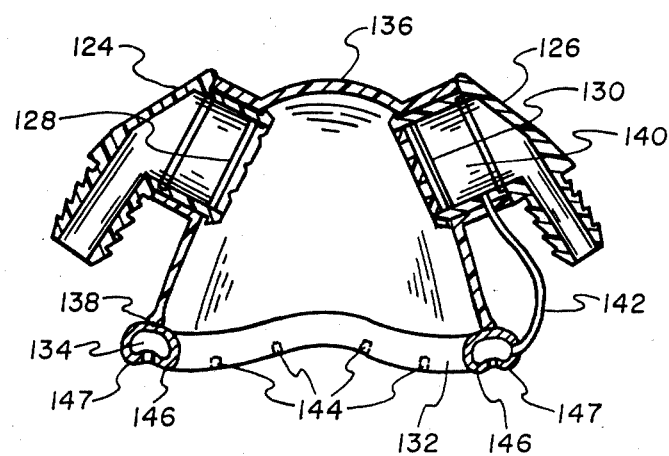
FIG. 17 is a section view of alternative embodiment of an anaesthetic mask of the invention.

FIG. 17 is a sectional view of an anaesthetic mask containing alternative features, which are not necessarily all combined in one embodiment of a mask. Inlet member 124 includes a valve 128, which may be a flapper valve, including a flapper spool such as illustrated in FIGS. 15 and 16. Valve 128 opens to allow the intake of anaesthetic gas only upon inhalation. Similar to other illustrated embodiments, outlet member 126 includes valve 130, which may also be a flapper valve, and which opens only upon exhalation.

The embodiment of FIG. 17 includes a seal 132 in which is formed a channel 134. In other embodiments, a scavenging channel is formed by the association between the seal and the respiratory chamber. However, in the embodiment of FIG. 17, a scavenging channel (channel 134) is formed in the face seal (seal 134) apart from its association with respiratory chamber 136. Seal 132 is connected to respiratory chamber 136 by means of an adhesive 138. The face seal 132 may be disposable.

In the other illustrated embodiments, gas intercommunication is provided between the interior channel and the outlet member by means of connection channel 18, formed in respiratory chamber 10. In the embodiment of FIG. 16, gas communication is provided between scavenging channel 134 and interior channel 140 of outlet member 126 by means of an exterior tube 142. Face seal 132 includes holes 144, which are positioned similarly to holes 50 in FIG. 2 i.e., between ridges 146 and 147 of seal 132, similar to seal 12. The space between ridges 146 and 147 define a scavenging channel, which is in addition to scavenging channel 134.

Figure 18:
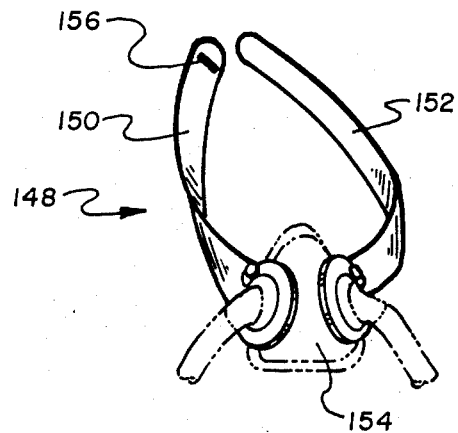
FIG. 18 is a perspective view of attachment straps of the invention and with other components shown in phantom lines.

FIG. 18 illustrates an advantageous strap for use with a mask of the invention. Strap 148 includes belts 150 and 152 connected to mask 154 at the inlet and outlet members, as shown. Strap 150 has a slit 156, which however, is not necessary for a proper functioning and use of strap 148. Belts 150 and 152 are typically formed of a flexible material having an adhering or a tacky exterior. A material known as Hi-Stat has been found to be particularly advantageous for this use.

Figure 19:
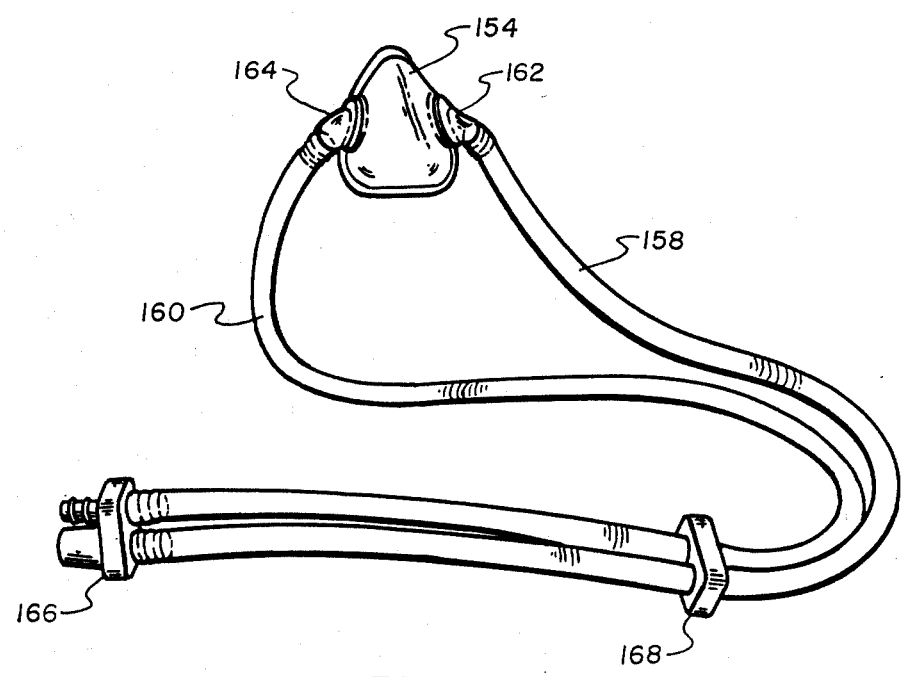
FIG. 19 is a perspective view of a hose arrangement of the invention.

FIG. 19 illustrates a mask 154, with an anaesthetic gas and vacuum hoses 158 and 160 connected to members 162 and 164 respectively, as shown. Hoses 158 and 160 are connected to a connecting fixture 166 and are held together by a bracket 168, as shown.

Reference herein to details of the illustrated embodiment is not intended to restrict the scope of the appended claims, which themselves recite those features regarded as essential to the invention.

What is claimed is:

1. An anaesthetic mask comprising:
   a wall forming a respiratory chamber having a rim sized and configured to generally conform to a selected area surrounding the nose and/or mouth of a patient, said rim having a closed-loop perimeter and a generally "Y"-shaped cross section;
   an anaesthetic gas inlet mechanically associated with said respiratory chamber for connection to an anaesthetic gas supply;
   an exhaust outlet mechanically associated with said respiratory chamber for connection with a vacuum supply;
   a face seal connected to said rim, said seal including:
      a closed-loop seal body defining a vacuum channel therein and further including a plurality of openings arranged to provide gas intercommunication between said vacuum channel and the exterior of said seal body, said seal body enclosing said rim and
      vacuum connection means for providing gas intercommunication between said vacuum channel and said vacuum supply.

2. The mask of claim 1, wherein said vacuum channel is formed by an interior tubular space between said seal body and said rim when said seal body is connected to said rim.

3. The mask of claim 2, wherein said vacuum connection means is formed by said mask having a vacuum connection channel formed in the wall of said respiratory chamber and opening in the proximity of said rim and said vacuum supply.

4. The mask of claim 1, wherein said seal body includes a plurality of sealing surfaces, at least one of which is sized and adapted to seal against the face of a patient and adjacent said sealing surfaces to define a secondary vacuum channel.

5. The mask of claim 4, wherein said sealing surfaces are sized and adapted to make contact with and seal against the face of a patient.

6. The mask of claim 4, wherein at least one of said plurality of openings provides gas intercommunication between said secondary channel and said vacuum channel.

7. The mask of claim 1, wherein said seal body is formed of a flexible, rubber-like material.

8. The mask of claim 1, wherein said seal body is removable from said mask.

9. The mask of claim 1, wherein said seal body is formed of a sterilizable material.

10. The mask of claim 1, wherein said inlet and said outlet are rotatably connected to said mask.

11. The mask of claim 1, having a strap with two belts which connect to said mask, said belts having means for connecting to each other.

12. The mask of claim 11, wherein one of said belts of said strap has a slot sized to receive the other of said belts.

13. The mask of claim 11, wherein one of said belts connects to said inlet and the other of said belts connects to said outlet.

14. The mask of claim 1, wherein said respiratory chamber is formed of a transparent material.

15. An anaesthetic mask, comprising:
   a wall forming a cup shaped respiratory chamber adapted to be placed on the face over the nose and/or mouth of a patient, said respiratory chamber having a closed-loop shaped rim sized and configured to generally conform to a patient's face when said mask is placed upon the nose and/or mouth area of a patient's face, said rim having a generally "Y"-shaped cross section;
   an anaesthetic gas inlet connected to said respiratory chamber for connection to an anaesthetic gas supply and to provide gas intercommunication between said gas supply and said respiratory chamber;
   a vacuum outlet connected to said respiratory chamber for connection to a vacuum supply to provide gas intercommunication between said vacuum supply and said respiratory chamber;
   a closed-loop seal body formed of a flexible rubber-like material being sized and configured to generally conform to said rim of said chamber to seal against a patient's face and having a closed-loop shaped channel which connects to said rim by means of said closed-loop shaped channel enclosing said rim, said rim air-tightly sealing said closed-loop shaped channel so that an interior tubular space between said closed-loop shaped channel and said rim forms a vacuum channel, said seal body having a plurality of openings to provide gas intercommunication between said vacuum channel and an exterior surface of said seal body; and
   a tube mechanically associated with said seal body and said vacuum supply to provide gas intercommunication between said vacuum channel and said vacuum supply.

16. The mask of claim 15, wherein said seal body has two closed-loop sealing surfaces sized and configured to make contact with and seal against a patient's face and having a secondary channel between said sealing surfaces and wherein at least one of said openings provides gas intercommunication between said secondary channel and said vacuum channel.

17. The mask of claim 15 wherein said tube is formed within the wall of said respiratory chamber and provides gas communication between said vacuum channel and said vacuum outlet.

18. The mask of claim 15, including valve means mechanically associated with said vacuum outlet to provide direct vacuum to said respiratory chamber only upon exhalation of a patient.

19. The mask of claim 18, wherein said tube is in open communication with said vacuum supply.

20. The mask of claim 15, having a strap having two belts, one of said belts being connected to said inlet and the other of said belts being connected to said outlet, said belts having means for connecting to each other.

21. The mask of claim 15, wherein said seal body may be removed from said respiratory chamber and wherein said seal body is formed of a sterilizable material.

22. The mask of claim 15, wherein said respiratory chamber is formed of a rigid transparent material.

* * * * *